(12) United States Patent
Ernst et al.

(10) Patent No.: US 11,241,652 B2
(45) Date of Patent: Feb. 8, 2022

(54) ABSORBENT AND PROCESS FOR SELECTIVELY REMOVING HYDROGEN SULFIDE

(71) Applicants: BASF SE, Ludwigshafen am Rhein (DE); ExxonMobil Research and Engineering Company, Annandale, NJ (US)

(72) Inventors: Martin Ernst, Ludwigshafen am Rhein (DE); Gerald Vorberg, Ludwigshafen am Rhein (DE); Georg Sieder, Ludwigshafen am Rhein (DE); Thomas Ingram, Ludwigshafen am Rhein (DE); Virginia Reiner, Summit, NJ (US); Carla Pereira, Bridgewater, NJ (US); Michael Siskin, Westfield, NJ (US)

(73) Assignees: BASF SE (REITSTÖTTER, KINZEBACH & PARTNER), Ludwigshafen am Rhein (DE); ExxonMobil Research and Engineering Company, Annandale, NJ (US)

( * ) Notice: Subject to any disclaimer, the term of this patent is extended or adjusted under 35 U.S.C. 154(b) by 251 days.

(21) Appl. No.: 16/612,921

(22) PCT Filed: May 14, 2018

(86) PCT No.: PCT/EP2018/062355
§ 371 (c)(1),
(2) Date: Nov. 12, 2019

(87) PCT Pub. No.: WO2018/210738
PCT Pub. Date: Nov. 22, 2018

(65) Prior Publication Data
US 2020/0164303 A1 May 28, 2020

(30) Foreign Application Priority Data

May 15, 2017 (EP) .................................... 17171012

(51) Int. Cl.
*B01D 53/14* (2006.01)
*C07C 13/02* (2006.01)
(Continued)

(52) U.S. Cl.
CPC ..... *B01D 53/1493* (2013.01); *B01D 53/1425* (2013.01); *B01D 53/1468* (2013.01);
(Continued)

(58) Field of Classification Search
CPC ................ C07C 213/02; C07C 217/08; B01D 2252/2025; B01D 2252/2026;
(Continued)

(56) References Cited

U.S. PATENT DOCUMENTS 4,417,075 A 11/1983 Stogryn
4,537,753 A 8/1985 Wagner et al.
(Continued)

FOREIGN PATENT DOCUMENTS

CA 1290553 C 10/1991
CA 1295810 C 2/1992
(Continued)

OTHER PUBLICATIONS

International Search Report for PCT/EP2018/062355 dated Jun. 20, 2018.
(Continued)

*Primary Examiner* — Cabrena Holecek
(74) *Attorney, Agent, or Firm* — Faegre Drinker Biddle & Reath LLP

(57) ABSTRACT

An absorbent for the selective removal of hydrogen sulfide from a fluid stream comprising carbon dioxide and hydrogen
(Continued)

sulfide, wherein the absorbent contains an aqueous solution, comprising: a) an amine or a mixture of amines of the general formula (I) wherein $R^1$ is $C_1$-$C_5$-alkyl; $R^2$ is $C_1$-$C_5$-alkyl; $R^3$ is selected from hydrogen and $C_1$-$C_5$-alkyl; x is an integer from 2 to 10; and b) an ether or a mixture of ethers of the general formula (II): $R^4$—[O—$CH_2$—$CH_2$]$_y$—OH; wherein $R^4$ is $C_1$-$C_5$-alkyl; and y is an integer from 2 to 10; wherein $R^1$ and $R^4$ are identical; wherein the mass ratio of b) to a) is from 0.08 to 0.5. The absorbent is suitable for the selective removal of hydrogen sulfide from a fluid stream comprising carbon dioxide and hydrogen sulfide. The absorbent has a reduced tendency for phase separation at temperatures falling within the usual range of regeneration temperatures for the aqueous amine mixtures and is easily obtainable.

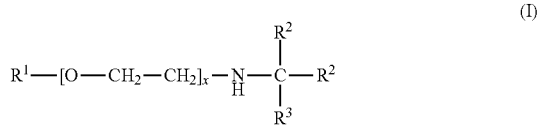

(I)

13 Claims, 7 Drawing Sheets

(51) Int. Cl.
| | | |
|---|---|---|
| *C07C 17/08* | (2006.01) | |
| *C10L 3/10* | (2006.01) | |
| *C07C 213/02* | (2006.01) | |
| *C07C 217/08* | (2006.01) | |

(52) U.S. Cl.
CPC .......... *C07C 213/02* (2013.01); *C07C 217/08* (2013.01); *C10L 3/103* (2013.01); *B01D 2252/2025* (2013.01); *B01D 2252/2026* (2013.01); *B01D 2252/20405* (2013.01); *B01D 2252/20426* (2013.01); *B01D 2252/504* (2013.01); *C10L 2290/12* (2013.01); *C10L 2290/541* (2013.01)

(58) Field of Classification Search
CPC ........... B01D 2252/20405; B01D 2252/20426; B01D 2252/20431; B01D 2252/504; B01D 2252/608; B01D 2257/30; B01D 2257/504; B01D 53/1425; B01D 53/1468; B01D 53/1493; C10L 2290/12; C10L 2290/541; C10L 3/103; C10L 3/104; Y02C 20/40; Y02P 20/151
See application file for complete search history.

(56) References Cited

U.S. PATENT DOCUMENTS

| | | |
|---|---|---|
| 4,551,158 A | 11/1985 | Wagner et al. |
| 4,553,984 A | 11/1985 | Volkamer et al. |
| 4,997,630 A | 3/1991 | Wagner et al. |
| 4,999,031 A | 3/1991 | Gerhardt et al. |
| 6,436,174 B1 | 8/2002 | Grossmann et al. |
| 8,486,183 B2 | 7/2013 | Siskin et al. |
| 8,487,135 B2 | 7/2013 | Kubanek et al. |
| 10,450,261 B2 | 10/2019 | Schaub et al. |
| 10,493,398 B2 | 12/2019 | Ingram et al. |
| 10,525,404 B2 | 1/2020 | Ingram et al. |
| 2013/0142717 A1 | 6/2013 | Siskin et al. |
| 2013/0243676 A1 | 9/2013 | Siskin et al. |
| 2015/0027055 A1 | 1/2015 | Kortunov et al. |
| 2018/0297926 A1 | 10/2018 | Schaub et al. |
| 2018/0311611 A1 | 11/2018 | Vorberg et al. |
| 2019/0126193 A1 | 5/2019 | Ingram et al. |
| 2019/0126194 A1 | 5/2019 | Ingram et al. |
| 2019/0143262 A1 | 5/2019 | Ingram et al. |

FOREIGN PATENT DOCUMENTS

| | | | |
|---|---|---|---|
| EP | 0121109 A2 | 10/1984 | |
| EP | 0159495 A2 | 10/1985 | |
| EP | 0190434 A3 | 8/1986 | |
| EP | 0202600 A2 | 11/1986 | |
| EP | 0359991 A1 | 3/1990 | |
| WO | WO-00000271 A1 | 1/2000 | |
| WO | WO-2007021462 A2 * | 2/2007 | ......... B01D 53/1493 |
| WO | WO-2011067199 A1 | 6/2011 | |
| WO | WO-2013181242 A1 | 12/2013 | |
| WO | WO-2013181245 A1 | 12/2013 | |
| WO | WO-2013181252 A1 | 12/2013 | |
| WO | WO-2015041914 A1 | 3/2015 | |

OTHER PUBLICATIONS

Written Opinion of the International Searching Authority for PCT/EP2018/062355 dated Jun. 20, 2018.
U.S. Appl. No. 15/781,555.
U.S. Appl. No. 16/594,526.
U.S. Appl. No. 16/074,100.
U.S. Appl. No. 16/463,186.
U.S. Appl. No. 16/464,495.
U.S. Appl. No. 16/484,860.

* cited by examiner

ABSORBENT AND PROCESS FOR SELECTIVELY REMOVING HYDROGEN SULFIDE

CROSS-REFERENCE TO RELATED APPLICATIONS

This application is a national stage application (under 35 U.S.C. § 371) of PCT/EP2018/062355, filed May 14, 2018, which claims benefit of European Application No. 17171012.2, filed May 15, 2017, both of which are incorporated herein by reference in their entirety.

The present invention relates to an absorbent suitable for the selective removal of hydrogen sulfide from a fluid stream comprising carbon dioxide and hydrogen sulfide. The present invention also relates to a process for obtaining the absorbent, and a process for selectively removing hydrogen sulfide from a fluid stream comprising hydrogen sulfide and carbon dioxide.

The removal of acid gases, for example $CO_2$, $H_2S$, $SO_2$, $CS_2$, HCN, COS or mercaptans, from fluid streams such as natural gas, refinery gas or synthesis gas is desirable for various reasons. Sulfur compounds in natural gas tend to form corrosive acids in particular together with the water frequently entrained by the natural gas. For the transport of the natural gas in a pipeline or further processing in a natural gas liquefaction plant (LNG=liquefied natural gas), given limits for the sulfur-containing impurities therefore have to be observed. In addition, numerous sulfur compounds are malodorous and toxic even at low concentrations.

Carbon dioxide has to be removed from natural gas because a high concentration of $CO_2$ reduces the calorific value of the gas. Moreover, $CO_2$ in conjunction with moisture can lead to corrosion in pipes and valves.

Known processes for removing acid gases include scrubbing operations with aqueous absorbent solutions of inorganic or organic bases. When acid gases are dissolved in the absorbent, ions form with the bases. The absorbent can be regenerated by decompression to a lower pressure and/or by stripping, whereby the ionic species react in reverse and the acid gases are released and/or stripped out by means of steam. After the regeneration process, the absorbent can be reused.

A process in which $CO_2$ and $H_2S$ are substantially removed is referred to as "total absorption". While removal of $CO_2$ may be necessary to avoid corrosion problems and provide the required heating value to the consumer, it is occasionally necessary or desirable to treat acid gas mixtures containing both $CO_2$ and $H_2S$ so as to remove the $H_2S$ selectively from the mixture while minimizing removal of the $CO_2$. Natural gas pipeline specifications, for example, set more stringent limits on the $H_2S$ level than on $CO_2$ since $H_2S$ is more toxic and corrosive than $CO_2$: common carrier natural gas pipeline specifications typically limit the $H_2S$ content to 4 ppmv with a more lenient limitation on the $CO_2$ at 2 vol %. Selective $H_2S$ removal is often desirable to enrich the $H_2S$ level in the feed to a sulfur recovery, such as a downstream Claus plant.

Severely sterically hindered secondary amines, such as 2-(2-tert-butylaminoethoxy)ethanol (TBAEE), and tertiary amines, such as methyldiethanolamine (MDEA), exhibit kinetic selectivity for $H_2S$ over $CO_2$. Such amines are therefore suitable for selective removal of $H_2S$ from gas mixtures comprising $CO_2$ and $H_2S$ and are generally utilized as aqueous mixtures. These amines do not react directly with $CO_2$; instead, $CO_2$ is reacted in a slow reaction with the amine and with water to give bicarbonate. The reaction kinetics allow $H_2S$ to react more rapidly with the amine groups of the sorbent to form a hydrosulfide salt in aqueous solution.

The use of hydroxyl-substituted amines (alkanolamines) such as those mentioned above has become common since the presence of the hydroxyl groups tends to improve the solubility of the absorbent/acid gas reaction products in the aqueous solvent systems widely used, so facilitating circulation of the solvent through the conventional absorber tower/regeneration tower unit by suppressing phase separation.

This preference may, however, present its own problems in certain circumstances. A current business incentive is to reduce the cost to regenerate and to recompress acid gases prior to sequestration. For natural gas systems, the separation of the acid gases can occur at pressures of about 2,000 to 15,000 kPaa, more typically from about 4,000 to 10,000 kPaa. While the alkanolamines will effectively remove acid gases at these pressures, the selectivity for $H_2S$ removal can be expected to decrease markedly both by direct physical absorption of the $CO_2$ in the liquid solvent and by reaction with the hydroxyl groups on the amine compound. Although the $CO_2$ reacts preferentially with the amino nitrogen, higher pressures force reaction with the oxygens and under the higher pressures, the bicarbonate/hemicarbonate/carbonate reaction product(s) formed by the reaction at the hydroxyl site is stabilized with a progressive loss in $H_2S$ selectivity with increasing pressure.

Further, while the presence of the hydroxyl groups improves the aqueous solubility of the amines, hydroxyl groups tend to impart surfactant properties to the absorbent/acid gas reaction products, thereby potentially causing troublesome foaming phenomena during the operation of the gas treatment unit.

Another known problem of using aqueous amine mixtures in the absorption treatment of gas mixtures is that separation into several phases may occur at temperatures falling within the range of regeneration temperatures for the aqueous amine mixtures, which is usually in the range of 50° C. to 170° C.

U.S. Pat. No. 8,486,183 describes an acid gas absorbent comprising an alkylamino alkyloxy monoalkyl ether and a process for the selective removal of $H_2S$ from gaseous mixtures containing $H_2S$ and $CO_2$ using an absorbent solution comprising an alkylamino alkyloxy alcohol monoalkyl ether.

US 2015/0027055 A1 describes a process for selectively removing $H_2S$ from a 002-containing gas mixture by means of an absorbent comprising sterically hindered, terminally etherified alkanolamines such as methoxyethoxyethoxyethanol-t-butylamine. It was found that the terminal etherification of the alkanolamines and the exclusion of water permit a higher $H_2S$ selectivity.

WO 2013/181242 A1 describes an absorbent composition useful in the selective removal of $H_2S$, wherein the absorbent composition includes an aqueous amine mixture of an amination reaction product of tert-butyl amine and a polyethylene glycol mixture, as well as an organic co-solvent, selected from sulfones, sulfone derivatives, and sulfoxides. It is stated that the organic co-solvent promotes the miscibility of the individual components of the aqueous amine mixture. WO 2013/181252 A1 describes a method for applying such an absorbent composition.

WO 2013/181245 A1 describes an absorbent composition useful in the selective removal of $H_2S$, wherein the absorbent composition includes an aqueous amine mixture of an amination reaction product of tert-butyl amine and a polyethylene glycol mixture, as well as an organic co-solvent, selected from sulfones, sulfone derivatives, and sulfoxides, and a strong acid to inhibit phase separation.

WO 2013/181252 A1 describes an absorbent composition useful in the selective removal of $H_2S$, wherein the absorbent composition includes an aqueous amine mixture of an amination reaction product of tert-butyl amine and a polyethylene glycol mixture, as well as an organic co-solvent, It is an object of the invention to provide further absorbents suitable for the selective removal of hydrogen sulfide from a fluid stream comprising carbon dioxide and hydrogen sulfide. The absorbents are to have a reduced tendency for phase separation at temperatures falling within the usual range of regeneration temperatures for the aqueous amine mixtures. The absorbents should be easily obtainable. A process for obtaining the absorbent and a process for selectively removing hydrogen sulfide from a fluid stream comprising carbon dioxide and hydrogen sulfide are also to be provided.

The object is achieved by an absorbent for the selective removal of hydrogen sulfide from a fluid stream comprising carbon dioxide and hydrogen sulfide, wherein the absorbent contains an aqueous solution, comprising:

a) an amine or a mixture of amines of the general formula (I)

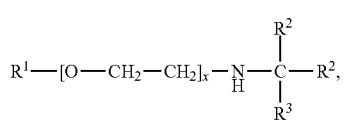

wherein $R^1$ is $C_1$-$C_5$-alkyl; $R^2$ is $C_1$-$C_5$-alkyl; $R^3$ is selected from hydrogen and $C_1$-$C_5$-alkyl; x is an integer from 2 to 10; and b) an ether or a mixture of ethers of the general formula (II);

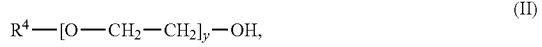

wherein $R^4$ is $C_1$-$C_5$-alkyl; and y is an integer from 2 to 10;

wherein $R^1$ and $R^4$ are identical;

wherein the mass ratio of b) to a) is from 0.08 to 0.5.

The ether compound b) comprises a terminal hydroxyl moiety. The presence of such hydroxyl compounds is believed to promote the miscibility of the individual components of the aqueous amine mixture. Thereby, the absorbents have a reduced tendency for phase separation at temperatures falling within the usual range of regeneration temperatures for the aqueous amine mixtures. The regeneration temperatures are normally in the range of 50° C. to 170° C., preferably 70° C. to 140° C., more preferred 110° C. to 135° C.

Surprisingly, it was found that the presence of the ether compound b) in an aqueous amine absorbent did not significantly decrease the selectivity of the absorbent for $H_2S$ over $CO_2$. Further, it was surprisingly found that the presence of the ether compound b) instead of alternative organic co-solvents, such as sulfolane, in some instances led to an improved selectivity for $H_2S$ over $CO_2$.

The absorbent preferably comprises 10% to 70% by weight, more preferably 15% to 65% by weight and most preferably 20% to 60% by weight of the amine a), based on the weight of the absorbent.

In one embodiment, component a) comprises a mixture of amines of the general formula (I) and/or component b) comprises a mixture of ethers of the general formula (II) wherein a) and/or b) have a molar ethoxylation distribution, i.e. the degree of ethoxylation x and y varies among the individual molecules of a) and/or among the individual molecules of b). In this case, it is preferred that the number average of x and the number average of y do not differ from each other by more than 1.0, preferably not more than 0.5.

In another embodiment, component a) is comprised of an amine of the general formula (I) with essentially uniform degree of ethoxylation; and component b) is comprised of an ether of the general formula (II) with essentially uniform degree of ethoxylation. In this case, it is preferred that x and y are identical. Most preferably, x and y are 3.

Preferably, the amine a) is selected from (2-(2-tert-butylaminoethoxy)ethyl)methyl ether, (2-(2-isopropylaminoethoxy)ethyl)methyl ether, (2-(2-(2-tert-butylaminoethoxy)-ethoxy)ethyl)methyl ether, (2-(2-(2-isopropylaminoethoxy)ethoxy)ethyl)methyl ether, (2-(2-(2-tert-butylaminoethoxy)ethoxy)ethoxy)ethyl)methyl ether, and (2-(2-(2-(2-Isopropylaminoethoxy)ethoxy)ethoxy)ethyl) methyl ether.

Preferably, the ether b) is selected from 2-(2-methoxyethoxy)ethanol, 2-(2-(2-methoxyethoxy)ethoxy)ethanol, and 2-(2-(2-(2-methoxyethoxy)ethoxy)ethoxy)ethanol.

In preferred embodiments, the amine a) is selected from (2-(2-tert-butylamino-ethoxy)ethyl)methyl ether, (2-(2-isopropylaminoethoxy)ethyl)methyl ether, (2-(2-(2-tert-butylaminoethoxy)ethoxy)ethyl)methyl ether, (2-(2-(2-isopropylaminoethoxy)ethoxy)-ethyl)methyl ether, (2-(2-(2-(2-tert-butylaminoethoxy)ethoxy)ethoxy)ethyl)methyl ether, and (2-(2-(2-Isopropylaminoethoxy)ethoxy)ethoxy)ethyl) methyl ether and the ether b) is selected from 2-(2-methoxyethoxy)ethanol, 2-(2-(2-methoxyethoxy)ethoxy)-ethanol, and 2-(2-(2-(2-methoxyethoxy)ethoxy)ethoxy)ethanol. It is especially preferred that the amine a) is (2-(2-(2-tert-butylaminoethoxy)ethoxy)ethyl)methyl ether (M3ETB) and the ether b) is 2-(2-(2-methoxyethoxy)ethoxy)ethanol (MTEG).

The mass ratio of ether b) to amine a) is from 0.08 to 0.5, preferably from 0.15 to 0.35.

In an embodiment, the absorbent comprises an acid c). The acid helps to regenerate the absorbent to low loadings and enhance the efficiency of the process. Protonation equilibria form between the acid c) and amine a). The position of the equilibria is temperature-dependent, and the equilibrium is shifted at higher temperatures toward the free oxonium ion and/or the amine salt having the lower enthalpy of protonation. At relatively low temperatures as prevail in the absorption step, the higher pH promotes efficient acid gas absorption, whereas, at relatively high temperatures as prevail in the desorption step, the lower pH supports the release of the absorbed acid gases.

Surprisingly, it was found that the presence of an acid in an absorbent of the invention may also lead to a higher $H_2S$-selectivity.

The acid c) preferably has a $pK_A$ of less than 6, especially less than 5, measured at 25° C. In the case of acids having more than one dissociation stage and accordingly more than one $pK_A$, this requirement is met where one of the $pK_A$ values is within the range specified. The acid is suitably selected from protic acids (Brønsted acids).

The acid is preferably added in such an amount that the pH of the aqueous solution measured at 120° C. is 7.9 to less than 9.5, preferably 8.0 to less than 8.8, more preferably 8.0 to less than 8.5, most preferably 8.0 to less than 8.2.

The amount of acid, in one embodiment, is 0.1% to 5.0% by weight, preferably 0.2% to 4.5% by weight, more preferably 0.5% to 4.0% by weight and most preferably 1.0% to 2.5% by weight, based on the weight of the absorbent.

The acid is selected from organic and inorganic acids. Suitable organic acids comprise, for example, phosphonic acids, sulfonic acids, carboxylic acids and amino acids. In particular embodiments, the acid is a polybasic acid.

Suitable acids are, for example, mineral acids such as hydrochloric acid, sulfuric acid, amidosulfuric acid, phosphoric acid, partial esters of phosphoric acid, for example mono- and dialkyl phosphates and mono- and diaryl phosphates such as tridecyl phosphate, dibutyl phosphate, diphenyl phosphate and bis(2-ethylhexyl) phosphate; boric acid;

carboxylic acids, for example saturated aliphatic monocarboxylic acids such as formic acid, acetic acid, propionic acid, butyric acid, isobutyric acid, valeric acid, isovaleric acid, pivalic acid, caproic acid, n-heptanoic acid, caprylic acid, 2-ethylhexanoic acid, pelargonic acid, capric acid, neodecanoic acid, undecanoic acid, lauric acid, tridecanoic acid, myristic acid, pentadecanoic acid, palmitic acid, margaric acid, stearic acid, isostearic acid, arachic acid, behenic acid; saturated aliphatic polycarboxylic acids such as oxalic acid, malonic acid, succinic acid, glutaric acid, adipic acid, pimelic acid, suberic acid, azelaic acid, sebacic acid, dodecanedioic acid; cycloaliphatic mono- and polycarboxylic acids such as cyclohexanecarboxylic acid, hexahydrophthalic acid, tetrahydrophthalic acid, resin acids, naphthenic acids; aliphatic hydroxycarboxylic acids such as glycolic acid, lactic acid, mandelic acid, hydroxybutyric acid, tartaric acid, malic acid, citric acid; halogenated aliphatic carboxylic acids such as trichloroacetic acid or 2-chloropropionic acid; aromatic mono- and polycarboxylic acids such as benzoic acid, salicylic acid, gallic acid, the positionally isomeric toluic acids, methoxybenzoic acids, chlorobenzoic acids, nitrobenzoic acids, phthalic acid, terephthalic acid, isophthalic acid; technical carboxylic acid mixtures, for example Versatic acids;

sulfonic acids such as methylsulfonic acid, butylsulfonic acid, 3-hydroxypropylsulfonic acid, sulfoacetic acid, benzenesulfonic acid, p-toluenesulfonic acid, p-xylenesulfonic acid, 4-dodecylbenzenesulfonic acid, 1-naphthalenesulfonic acid, dinonylnaphthalene-sulfonic acid and dinonylnaphthalenedisulfonic acid, trifluoromethyl- or nonafluoro-n-butylsulfonic acid, camphorsulfonic acid, 2-(4-(2-hydroxyethyl)-1-piperazinyl)-ethanesulfonic acid (HEPES);

organic phosphonic acids, for example phosphonic acids of the formula (IV)

$$R^5-PO_3H \quad (IV)$$

in which $R^5$ is $C_{1-18}$-alkyl optionally substituted by up to four substituents independently selected from carboxyl, carboxamido, hydroxyl and amino.

These include alkylphosphonic acids such as methylphosphonic acid, propylphosphonic acid, 2-methylpropylphosphonic acid, t-butylphosphonic acid, n-butylphosphonic acid, 2,3-dimethylbutylphosphonic acid, octylphosphonic acid; hydroxyalkylphosphonic acids such as hydroxymethylphosphonic acid, 1-hydroxyethylphosphonic acid, 2-hydroxyethylphosphonic acid; arylphosphonic acids such as phenylphosphonic acid, tolylphosphonic acid, xylylphosphonic acid, amino-alkylphosphonic acids such as aminomethylphosphonic acid, 1-aminoethylphosphonic acid, 1-dimethylaminoethylphosphonic acid, 2-aminoethylphosphonic acid, 2-(N-methylamino)ethylphosphonic acid, 3-aminopropylphosphonic acid, 2-aminopropylphosphonic acid, 1-aminopropylphosphonic acid, 1-aminopropyl-2-chloropropylphosphonic acid, 2-aminobutylphosphonic acid, 3-aminobutylphosphonic acid, 1-aminobutylphosphonic acid, 4-aminobutylphosphonic acid, 2-aminopentylphosphonic acid, 5-aminopentylphosphonic acid, 2-aminohexylphosphonic acid, 5-aminohexylphosphonic acid, 2-aminooctylphosphonic acid, 1-aminooctylphosphonic acid, 1-aminobutylphosphonic acid; amidoalkylphosphonic acids such as 3-hydroxymethylamino-3-oxopropylphosphonic acid; and phosphonocarboxylic acids such as 2-hydroxyphosphonoacetic acid and 2-phosphonobutane-1,2,4-tricarboxylic acid;

phosphonic acids of the formula (V)

in which $R^6$ is H or $C_{1-6}$-alkyl, Q is H, OH or $NR^7_2$ and $R^7$ is H or $CH_2PO_3H_2$, such as 1-hydroxyethane-1,1-diphosphonic acid;

phosphonic acids of the formula (VI)

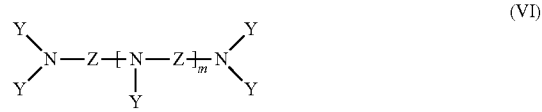

in which Z is $C_{2-6}$-alkylene, cycloalkanediyl, phenylene, or $C_{2-6}$-alkylene interrupted by cycloalkanediyl or phenylene, Y is $CH_2PO_3H_2$ and m is 0 to 4, such as ethylenediaminetetra(methylenephosphonic acid), diethylenetriaminepenta(methylenephosphonic acid) and bis(hexamethylene)triaminepenta(methylenephosphonic acid);

phosphonic acids of the formula (VII)

$$R^8-NY_2 \quad (VII)$$

in which $R^8$ is $C_{1-6}$-alkyl, $C_{2-6}$-hydroxyalkyl or $R^9$, and $R^9$ is $CH_2PO_3H_2$, such as nitrilotris(methylenephosphonic acid) and 2-hydroxyethyliminobis(methylenephosphonic acid);

aminocarboxylic acids having tertiary amino groups or amino groups having at least one secondary or tertiary carbon atom immediately adjacent to the amino group, such as α-amino acids having tertiary amino groups or amino groups having at least one secondary or tertiary carbon atom immediately adjacent to the amino group, such as N,N-dimethylglycine (dimethylaminoacetic acid), N,N-diethylglycine, alanine (2-aminopropionic acid), N-methylalanine (2-(methylamino)propionic acid), N,N-dimethylalanine, N-ethylalanine, 2-methylalanine (2-aminoisobutyric acid), leucine (2-amino-4-methylpentan-1-oic acid), N-methylleucine, N,N-dimethylleucine, isoleucine (1-amino-2-methylpentanoic acid), N-methylisoleucine, N,N-dimethylisoleucine, valine (2-aminoisovaleric acid), α-methylvaline (2-amino-2-methylisovaleric acid), N-methylvaline (2-methylaminoisovaleric acid), N,N-dimethylvaline, proline (pyrrolidine-2-carboxylic acid), N-methylproline, N-methylserine, N,N-dimethylserine, 2-(methylamino) isobutyric acid, piperidine-2-carboxylic acid, N-methylpiperidine-2-carboxylic acid, β-amino acids having tertiary amino groups or amino groups having at least one secondary or tertiary carbon atom immediately adjacent to the amino group, such as 3-dimethylaminopropionic acid, N-methyliminodipropionic acid, N-methylpiperidine-3-carboxylic acid, γ-amino acids having tertiary amino groups or amino groups having at least one secondary or tertiary carbon atom immediately adjacent to the amino group, such as 4-dimethylaminobutyric acid, or aminocarboxylic acids having tertiary amino groups or amino groups having at least one secondary or tertiary carbon atom immediately adjacent to the amino group, such as N-methylpiperidine-4-carboxylic acid.

Among the inorganic acids, preference is given to phosphoric acid and sulfuric acid, especially sulfuric acid.

Among the carboxylic acids, preference is given to formic acid, acetic acid, benzoic acid, succinic acid and adipic acid.

Among the sulfonic acids, preference is given to methanesulfonic acid, p-toluenesulfonic acid and 2-(4-(2-hydroxyethyl)-1-piperazinyl)ethanesulfonic acid (HEPES).

Among the phosphonic acids, preference is given to 2-hydroxyphosphonoacetic acid, 2-phosphonobutane-1,2,4-tricarboxylic acid, 1-hydroxyethane-1,1-diphosphonic acid, ethylenediaminetetra(methylenephosphonic acid), diethylenetriaminepenta-(methylenephosphonic acid), bis(hexamethylene)triaminepenta(methylenephosphonic acid) (HDTMP) and nitrilotris(methylenephosphonic acid), among which 1-hydroxyethane-1,1-diphosphonic acid is particularly preferred.

Among the aminocarboxylic acids having tertiary amino groups or amino groups having at least one secondary or tertiary carbon atom immediately adjacent to the amino group, preference is given to N,N-dimethylglycine and N-methylalanine.

More preferably, the acid is an inorganic acid.

In one embodiment, the absorbent comprises a tertiary amine or severely sterically hindered primary amine and/or severely sterically hindered secondary amine other than the compounds of the general formula (I). Severe steric hindrance is understood to mean a tertiary carbon atom directly adjacent to a primary or secondary nitrogen atom. In this embodiment, the absorbent comprises the tertiary amine or severely sterically hindered amine other than the compounds of the general formula (I) generally in an amount of 5% to 50% by weight, preferably 10% to 40% by weight and more preferably 20% to 40% by weight, based on the weight of the absorbent.

The suitable tertiary amines especially include:

1. Tertiary alkanolamines such as
bis(2-hydroxyethyl)methylamine (methyldiethanolamine, MDEA), tris(2-hydroxyethyl)amine (triethanolamine, TEA), tributanolamine, 2-diethylaminoethanol (diethylethanolamine, DEEA), 2-dimethylaminoethanol (dimethylethanolamine, DMEA), 3-dimethylamino-1-propanol (N,N-dimethylpropanolamine), 3-diethylamino-1-propanol, 2-diisopropylaminoethanol (DI EA), N,N-bis(2-hydroxypropyl)methylamine (methyldiisopropanolamine, MDIPA);

2. Tertiary amino ethers such as
3-methoxypropyldimethylamine;

3. Tertiary polyamines, for example bis-tertiary diamines such as
N,N,N',N'-tetramethylethylenediamine, N,N-diethyl-N',N'-dimethylethylenediamine, N,N,N',N'-tetraethylethylenediamine, N,N,N',N'-tetramethyl-1,3-propanediamine (TMPDA), N,N,N',N'-tetraethyl-1,3-propanediamine (TEPDA), N,N,N',N'-tetramethyl-1,6-hexanediamine, N,N-dimethyl-N',N'-diethylethylenediamine (DMDEEDA), 1-dimethylamino-2-dimethylaminoethoxyethane (bis[2-(dimethylamino)ethyl] ether), 1,4-diazabicyclo[2.2.2]octane (TEDA), tetramethyl-1,6-hexanediamine;

and mixtures thereof.

Tertiary alkanolamines, i.e. amines having at least one hydroxyalkyl group bonded to the nitrogen atom, are generally preferred. Particular preference is given to methyldiethanolamine (MDEA).

The suitable highly sterically hindered amines (i.e. amines having a tertiary carbon atom directly adjacent to a primary or secondary nitrogen atom) other than the compounds of the general formula (I) especially include:

1. Severely sterically hindered secondary alkanolamines such as
2-(2-tert-butylaminoethoxy)ethanol (TBAEE), 2-(2-tert-butylamino)propoxyethanol, 2-(2-tert-amylaminoethoxy) ethanol, 2-(2-(1-methyl-1-ethylpropylamino)ethoxy)ethanol, 2-(tert-butylamino)ethanol, 2-tert-butylamino-1-propanol, 3-tert-butylamino-1-propanol, 3-tert-butylamino-1-butanol, and 3-aza-2,2-dimethylhexane-1,6-diol, 2-N-methylaminopropan-1-ol, 2-N-methylamino-2-methylpropan-1-ol;

2. Severely sterically hindered primary alkanolamines such as
2-amino-2-methylpropanol (2-AMP); 2-amino-2-ethylpropanol; and 2-amino-2-propylpropanol;

3. Severely sterically hindered amino ethers such as
1,2-bis(tert-butylaminoethoxy)ethane, bis(tert-butylaminoethyl) ether;

and mixtures thereof.

Severely sterically hindered secondary alkanolamines are generally preferred. Particular preference is given to 2-(2-tert-butylaminoethoxy)ethanol and 2-(2-tert-butylaminoethoxyethoxy)ethanol.

Generally the absorbent does not comprise any sterically unhindered primary amine or sterically unhindered secondary amine. A sterically unhindered primary amine is understood to mean compounds having primary amino groups to which only hydrogen atoms or primary or secondary carbon atoms are bonded. A sterically unhindered secondary amine is understood to mean compounds having secondary amino groups to which only hydrogen atoms or primary carbon atoms are bonded. Sterically unhindered primary amines or sterically unhindered secondary amines act as strong activators of $CO_2$ absorption. Their presence in the absorbent can result in loss of the $H_2S$ selectivity of the absorbent.

The absorbent may also comprise additives such as corrosion inhibitors, enzymes, antifoams, etc. In general, the amount of such additives is in the range from about 0.005% to 3% by weight of the absorbent.

Amines a) are obtainable by a process wherein an ether of the general formula (II)

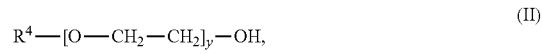

$$R^4-[O-CH_2-CH_2]_y-OH, \quad (II)$$

as described above, is reacted with a primary amine of the general formula (III)

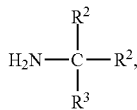

(III)

wherein $R^2$ is $C_1$-$C_5$-alkyl and $R^3$ is selected from hydrogen and $C_1$-$C_5$-alkyl; to form an amine of the general formula (I). Even though the primary amine of the general formula (III) is generally used in excess over the ether of the general formula (II), a complete conversion of the ether is difficult to obtain. Attempts to drive the conversion of the ether of the general formula (II) to completion by long reaction times and/or elevated temperatures resulted in the excessive formation of degradation products. On the other hand, the amine of the general formula (I) and the unreacted ether of the general formula (II) are difficult to separate, e.g., by distillation.

The invention thus provides a process for the production of an absorbent, comprising the reaction of an ether of formula (II) as defined above, with a primary amine of the general formula (III)

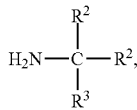

(III)

wherein $R^2$ is $C_1$-$C_5$-alkyl and $R^3$ is selected from hydrogen and $C_1$-$C_5$-alkyl;

to form an amine of formula (I), wherein the ether of formula (II) is not completely consumed in the reaction and the ether of formula (II) is not fully separated from the amine of formula (I). In the process of the invention, the ether of formula (II) is not completely consumed in the reaction and the ether of formula (II) is not fully separated from the amine of formula (I). Advantageously, the process allows for the production of an absorbent of the invention in a reaction comprising only one reaction step and a limited amount of work-up.

Preferably, the primary amine of formula (III) is used in molar excess over the molar amount of the ether of formula (II) during the reaction. In a preferred embodiment, the molar amount of the primary amine of formula (III) exceeds the molar amount of the ether of formula (II) at the start of the reaction by 5 to 5,000 mol-%, preferably 50 to 1,000 mol-%, based on the amount of the ether of formula (II).

Preferably, the reaction is carried out in the presence of a hydrogenation/dehydrogenation catalyst, for example in the presence of a copper-containing hydrogenation/dehydrogenation catalyst. The catalyst may be applied to a support, for example an alumina support.

In one embodiment, a supported copper-, nickel- and cobalt-containing hydrogenation/dehydrogenation catalyst is used, wherein the catalytically active material of the catalyst, before the reduction thereof with hydrogen, comprises oxygen compounds of aluminum, of copper, of nickel and of cobalt, and in the range from 0.2 to 5.0% by weight of oxygen compounds of tin, calculated as SnO. In a preferred embodiment, a catalyst according to the catalysts claimed in WO 2011/067199 is used, particularly a catalyst according to WO 2011/067199, example 5.

In a preferred embodiment, the reaction is carried out at a temperature of 150 to 260° C. In an especially preferred embodiment, the reaction is carried out at a temperature of 170 to 240° C. In a most preferred embodiment, the reaction is carried out at a temperature of 190 to 220° C.

The reaction may be carried out at pressures from 5 to 300 bar, in liquid or vapor phase. In a preferred embodiment, the reaction is carried out at a pressure of 60 to 200 bar (abs.). In an especially preferred embodiment, the reaction is carried out at a pressure of 70 to 130 bar (abs.).

The reaction may be carried out using stirred tank reactors, fixed bed tube reactors and multitube reactors. It may be carried out in batch, semi-batch and continuous mode and with and without recycling of the crude reaction mixture. In a preferred embodiment, the reaction is carried out in continuous mode in a fixed bed tube reactor.

The catalyst load may be varied in the range of 0.01 to 2 kg/(L·h), preferably in the range of 0.1 to 1.0 kg/(L·h), and in an especially preferred embodiment in the range of 0.2 to 0.8 kg/(L·h) of ether of formula (II).

In a preferred embodiment, excess primary amine (III) is separated from the product of the reaction by one-step distillation. The term "one-step distillation" is understood to mean a distillation with only a single separating stage, as is the case in a simple distillation setup where vapor generated in a reboiler is immediately channeled into a condenser. Contrarily, rectification columns, e.g., have several separating stages and represent a fractional distillation. Preferably, the separated excess primary amine (III) is recycled to the further production of the amine (I).

Besides the amine (I), the ether (II) and the primary amine (III), the reaction product contains several other substances. Usually, the reaction product contains water and side-products such as glycol diether(s), i.e., triethylene glycol dimethyl ether (triglyme) or diethylene glycol dimethyl ether (diglyme) when ether b) comprises 2-(2-(2-methoxyethoxy)ethoxy)ethanol (MTEG).

In a preferred embodiment, water and glycol diether are separated from the product of the reaction. In an especially preferred embodiment, water and glycol diether, as well as excess primary amine (III) still remaining in the reaction product after the one-step distillation described above, are removed from the reaction product by a second one-step distillation. This step is preferably done at a pressure of about 90 mbara. Any suited reboiler can be applied for this step. A falling film evaporator or thin film evaporator can be used. Particularly, thin film evaporation using a "Sambay" type evaporator may be applied and the generated gas is condensed at room temperature.

After the work-up steps, the obtained product may be mixed with water in order to obtain an absorbent of the invention. Further substances, as described above, may be added.

Alternatively, after the work-up steps, the obtained product may be transported to a site of utilization of acid gas absorbents, such as a gas scrubbing plant, and mixed with water on-site to obtain an absorbent of the invention. Further substances, as described above, may be added on-site.

Further provided is a process for the selective removal of hydrogen sulfide from a fluid stream comprising carbon dioxide and hydrogen sulfide, in which the fluid stream is contacted with an absorbent as in any of the embodiments described above, wherein a laden absorbent and a treated fluid stream are obtained.

In the present context, "selectivity for hydrogen sulfide" is understood to mean the value of the following quotient:

$$\frac{\frac{\text{mol }(H_2S)}{\text{mol }(CO_2)}(\text{liquid phase})}{\frac{\text{mol }(H_2S)}{\text{mol }(CO_2)}(\text{gas phase})} \text{ where } \frac{\text{mol }(H_2S)}{\text{mol }(CO_2)}(\text{liquid phase})$$

is the molar $H_2S/CO_2$ ratio in a liquid phase which is in contact with a gas phase and $$\frac{\text{mol }(H_2S)}{\text{mol }(CO_2)}(\text{gas phase})$$

is the molar $H_2S/CO_2$ ratio in the gas phase. In a standard gas scrubbing process, the liquid phase is the laden absorbent at the bottom of the absorber and the gas phase is the fluid stream to be treated.

Surprisingly, it was found that the absorbent of the invention shows selectivity for $H_2S$ over $CO_2$ comparable to that of an aqueous solution of amine a). This was unexpected, as the presence of hydroxyl compounds such as ether b) usually leads to a decrease in $H_2S$-selectivity due to the reaction of $CO_2$ with the oxygen of the hydroxyl moiety. This is especially true under higher pressures, as may be applied during the treatment of fluids under high pressure, such as natural gas.

The absorbent of the invention is suitable for treatment of all kinds of fluids. Fluids are firstly gases such as natural gas, synthesis gas, coke oven gas, cracking gas, coal gasification gas, cycle gas, landfill gases and combustion gases, and secondly liquids that are essentially immiscible with the absorbent, such as LPG (liquefied petroleum gas) or NGL (natural gas liquids). The process of the invention is particularly suitable for treatment of hydrocarbonaceous fluid streams. The hydrocarbons present are, for example, aliphatic hydrocarbons such as $C_1$-$C_4$ hydrocarbons such as methane, unsaturated hydrocarbons such as ethylene or propylene, or aromatic hydrocarbons such as benzene, toluene or xylene.

The absorbent is suitable for the selective removal of hydrogen sulfide from a fluid stream comprising carbon dioxide and hydrogen sulfide and allows high $H_2S$ cleanup selectively at low solvent circulation rates. The absorbent is useful in sulfur plant Tail Gas Treating Unit (TGTU) applications, in Acid-Gas Enrichment (AGE) processes to upgrade lean acid offgas from treating units to higher-quality Claus plant feed, or for the treatment of associated gases and refinery gases.

Besides the selective removal of $H_2S$, further acid gases which may be present in the fluid stream, for example $SO_3$, $SO_2$, $CS_2$, HCN, COS and mercaptans, may also be removed.

In the process of the invention, the fluid stream is contacted with the absorbent in an absorption step in an absorber, as a result of which carbon dioxide and hydrogen sulfide are at least partly scrubbed out. This yields a $CO_2$— and $H_2S$-depleted fluid stream and a $CO_2$— and $H_2S$-laden absorbent.

The absorber used is a scrubbing apparatus used in customary gas scrubbing processes. Suitable scrubbing apparatuses are, for example, random packings, columns having structured packings and having trays, membrane contractors, radial flow scrubbers, jet scrubbers, Venturi scrubbers and rotary spray scrubbers, preferably columns having structured packings, having random packings and having trays, more preferably columns having trays and having random packings. The fluid stream is preferably treated with the absorbent in a column in countercurrent. The fluid is generally fed into the lower region and the absorbent into the upper region of the column. Installed in tray columns are sieve trays, bubble-cap trays or valve trays, over which the liquid flows. Columns having random packings can be filled with different shaped bodies. Heat and mass transfer are improved by the increase in the surface area caused by the shaped bodies, which are usually about 25 to 80 mm in size. Known examples are the Raschig ring (a hollow cylinder), Pall ring, Hiflow ring, Intalox saddle and the like. The random packings can be introduced into the column in an ordered manner, or else randomly (as a bed). Possible materials include glass, ceramic, metal and plastics. Structured packings are a further development of ordered random packings. They have a regular structure. As a result, it is possible in the case of packings to reduce pressure drops in the gas flow. There are various designs of structured packings, for example woven packings or sheet metal packings. Materials used may be metal, plastic, glass and ceramic.

The temperature of the absorbent in the absorption step is generally about 30 to 100° C., and when a column is used is, for example, 30 to 70° C. at the top of the column and 50 to 100° C. at the bottom of the column.

The process of the invention may comprise one or more, especially two, successive absorption steps. The absorption can be conducted in a plurality of successive component steps, in which case the crude gas comprising the acidic gas constituents is contacted with a substream of the absorbent in each of the component steps. The absorbent with which the crude gas is contacted may already be partly laden with acidic gases, meaning that it may, for example, be an absorbent which has been recycled from a downstream absorption step into the first absorption step, or be partly regenerated absorbent. With regard to the performance of the two-stage absorption, reference is made to publications EP 0 159 495, EP 0 190 434, EP 0 359 991 and WO 00100271.

The person skilled in the art can achieve a high level of hydrogen sulfide removal with a defined selectivity by varying the conditions in the absorption step, such as, more particularly, the absorbent/fluid stream ratio, the column height of the absorber, the type of contact-promoting internals in the absorber, such as random packings, trays or structured packings, and/or the residual loading of the regenerated absorbent.

Since $CO_2$ is absorbed more slowly than $H_2S$, more $CO_2$ is absorbed in a longer residence time than in a shorter residence time. Conversely, longer residence times tend to decrease $H_2S$ selectivity. A higher column therefore brings about a less selective absorption. Trays or structured packings with relatively high liquid holdup likewise lead to a less selective absorption. The heating energy introduced in the regeneration can be used to adjust the residual loading of the regenerated absorbent. A lower residual loading of regenerated absorbent leads to improved absorption.

The process preferably comprises a regeneration step in which the $CO_2$— and $H_2S$-laden absorbent is regenerated. In the regeneration step, $CO_2$ and $H_2S$ and optionally further acidic gas constituents are released from the $CO_2$— and $H_2S$-laden absorbent to obtain a regenerated absorbent. Preferably, the regenerated absorbent is subsequently recycled into the absorption step. In general, the regeneration step comprises at least one of the measures of heating, decompressing and stripping with an inert fluid.

The regeneration step preferably comprises heating of the absorbent laden with the acidic gas constituents, for example by means of a boiler, natural circulation evaporator, forced circulation evaporator or forced circulation flash evaporator. The absorbed acid gases are stripped out by means of the steam obtained by heating the solution. Rather than steam, it is also possible to use an inert fluid such as nitrogen. The absolute pressure in the desorber is normally 0.1 to 3.5 bar, preferably 1.0 to 2.5 bar. The temperature is normally of 50° C. to 170° C., preferably 70° C. to 140° C., more preferred 110° C. to 135° C. The regeneration temperature depends on the regeneration pressure.

The regeneration step may alternatively or additionally comprise a decompression. This includes at least one decompression of the laden absorbent from a high pressure as exists in the conduction of the absorption step to a lower pressure. The decompression can be accomplished, for example, by means of a throttle valve and/or a decompression turbine. Regeneration with a decompression stage is described, for example, in publications U.S. Pat. Nos. 4,537,753 and 4,553,984.

The acidic gas constituents can be released in the regeneration step, for example, in a decompression column, for example a flash vessel installed vertically or horizontally, or a countercurrent column with internals.

The regeneration column may likewise be a column having random packings, having structured packings or having trays. The regeneration column, at the bottom, has a heater, for example a forced circulation evaporator with circulation pump. At the top, the regeneration column has an outlet for the acid gases released. Entrained absorption medium vapors are condensed in a condenser and recirculated to the column.

It is possible to connect a plurality of decompression columns in series, in which regeneration is effected at different pressures. For example, regeneration can be effected in a preliminary decompression column at a high pressure typically about 1.5 bar above the partial pressure of the acidic gas constituents in the absorption step, and in a main decompression column at a low pressure, for example 1 to 2 bar absolute. Regeneration with two or more decompression stages is described in publications U.S. Pat. Nos. 4,537,753, 4,553,984, EP 0 159 495, EP 0 202 600, EP 0 190 434 and EP 0 121 109.

The invention is illustrated in detail by the appended drawings and the examples which follow.

Figure 1:
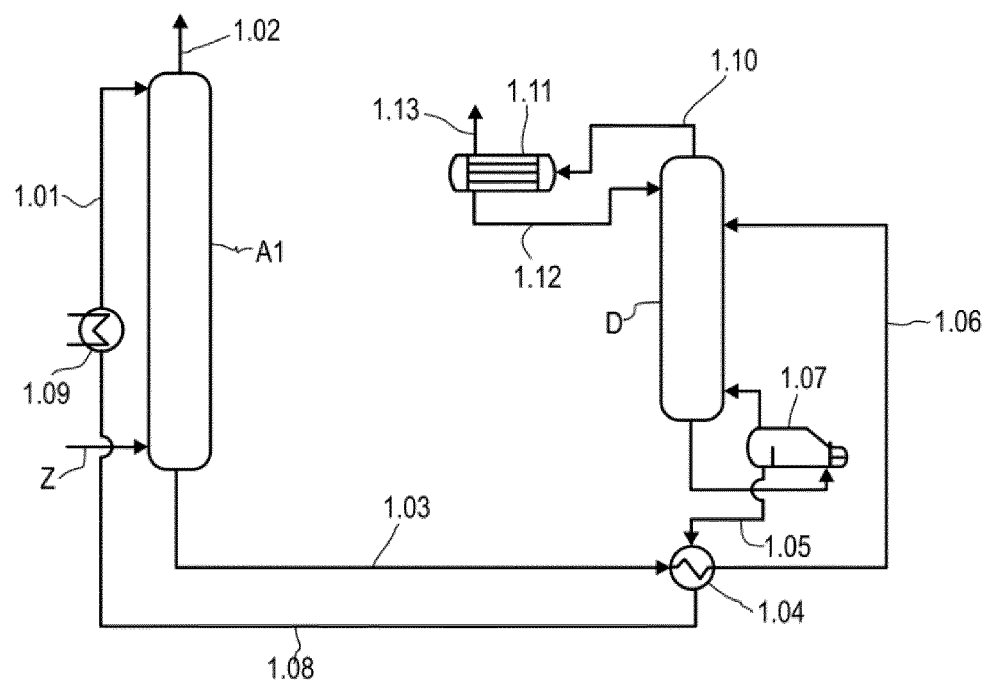
FIG. 1 is a schematic diagram of a plant suitable for performing the process of the invention.

According to FIG. 1, via the inlet Z, a suitably pre-treated gas comprising hydrogen sulfide and carbon dioxide is contacted in countercurrent, in an absorber A1, with regenerated absorbent which is fed in via the absorbent line 1.01. The absorbent removes hydrogen sulfide and carbon dioxide from the gas by absorption; this affords a hydrogen sulfide- and carbon dioxide-depleted clean gas via the offgas line 1.02.

Via the absorbent line 1.03, the heat exchanger 1.04 in which the $CO_2$— and $H_2S$-laden absorbent is heated up with the heat from the regenerated absorbent conducted through the absorbent line 1.05, and the absorbent line 1.06, the $CO_2$— and $H_2S$-laden absorbent is fed to the desorption column D and regenerated.

Between the absorber A1 and heat exchanger 1.04, one or more flash vessels may be provided (not shown in FIG. 1), in which the $CO_2$— and $H_2S$-laden absorbent is decompressed to, for example, 3 to 15 bar.

From the lower part of the desorption column D, the absorbent is conducted into the boiler 1.07, where it is heated. The steam that arises is recycled into the desorption column D, while the regenerated absorbent is fed back to the absorber A1 via the absorbent line 1.05, the heat exchanger 1.04 in which the regenerated absorbent heats up the $CO_2$— and $H_2S$-laden absorbent and at the same time cools down itself, the absorbent line 1.08, the cooler 1.09 and the absorbent line 1.01. Instead of the boiler shown, it is also possible to use other heat exchanger types for energy introduction, such as a natural circulation evaporator, forced circulation evaporator or forced circulation flash evaporator. In the case of these evaporator types, a mixed-phase stream of regenerated absorbent and steam is returned to the bottom of desorption column D, where the phase separation between the vapour and the absorbent takes place. The regenerated absorbent to the heat exchanger 1.04 is either drawn off from the circulation stream from the bottom of the desorption column D to the evaporator or conducted via a separate line directly from the bottom of the desorption column D to the heat exchanger 1.04.

The $CO_2$— and $H_2S$-containing gas released in desorption column D leaves the desorption column D via the offgas line 1.10. It is conducted into a condenser with integrated phase separation 1.11, where it is separated from entrained absorbent vapour. In this and all the other plants suitable for performance of the process of the invention, condensation and phase separation may also be present separately from one another. Subsequently, the condensate is conducted through the absorbent line 1.12 into the upper region of desorption column D, and a $CO_2$— and $H_2S$-containing gas is discharged via the gas line 1.13.

In the description of the examples, the following abbreviations were used:
M3ETB: (2-(2-(2-tert-butylaminoethoxy)ethoxy)ethyl) methyl ether
MTEG: 2-(2-(2-methoxyethoxy)ethoxy)ethanol
TBA: tert-butylamine

EXAMPLE 1: PREPARATION OF AN ABSORBENT COMPRISING (2-(2-(2-TERT-BUTYLAMINOETHOXY)-ETHOXY)ETHYL)METHYL ETHER (M3ETB)

A 1.4 L high pressure tubular reactor (length 2,000 mm, diameter 30 mm, equipped with an axially placed temperature probe with a diameter of 5 mm) with oil heating mantle, connected to a high pressure inlet for $H_2$ and $N_2$, as well as liquid MTEG and TBA feed lines equipped with high pressure pumps, and a high pressure and low pressure phase separator and sampling station downstream to the reactor, was filled stepwise with 500 mL ceramic balls, 500 mL amination catalyst (containing Ni, Co, Cu, Sn on $Al_2O_3$ and obtained according to WO 2011/067199, example 5) and 400 mL ceramic balls. The reactor was closed and air was displaced by $N_2$. Subsequently, the catalyst was activated by passing 400 standard L/h $H_2$ at 280° C. and ambient pressure for 24 h. After 24 h, the reactor was cooled to 50° C. and the $H_2$-pressure was increased to 200 bar with a flow rate of 100 standard L/h $H_2$. Then, the temperature was raised to 100° C. and dosage of TBA was started. The TBA flow rate was increased step-wise to 600 g/h. When the TBA load was stable, MTEG was initially pumped into the reactor at a flow rate of 51 g/L. Gradually over several days, the catalyst load was increased to 0.3 kg/(L·h) MTEG, while TBA load was adjusted to 0.4 kg/(L·h), which corresponds to a molar ratio of 6:1 TBA:MTEG. Temperature was set to 225° C. The reaction output was analyzed by means of gas chromatography (column: 30 m Rtx-5 Amine by Restek, internal diameter: 0.32 mm, $d_f$: 1.5 µm, temperature program 60° C. to 280° C. in steps of 5° C./min). The following analysis values are reported in GC area percent (for retention times $t_R$ cf. table). Conversion was 99.2%, and the sample contained 96.3% M3ETB (calculated as TBA-free) which corresponds to a selectivity of 97%. An aliquot of the collected reaction mixture was collected for distillation.

TBA was removed to a large extent under ambient pressure using a rotary evaporator at 90° C. bath temperature. 3.5 kg of the remaining crude product comprising 13.26 vol.-% TBA, 1.01 vol.-% MTEG, 82.62 vol.-% M3ETB and 3.11 vol.-% of other compounds were charged into a 4 L glass vessel and distilled over a column of 1,000 mm length with a diameter of 40 mm filled with Pall rings. 16 fractions were taken. The first fractions consisted of TBA, as determined from their boiling point. Fractions 7 to 16 (1,900 g) were combined. The purity of this sample was 99.8%.

| No. of fraction | boiling point [° C.] | pressure [mbar] | mass [g] | TBA ($t_R$ 3.45 min)* | MTEG ($t_R$ 25.88 min)* | M3ETB ($t_R$ 31.65 min)* | Other |
|---|---|---|---|---|---|---|---|
| 1 | 20-90 | 10 | 265 | | no GC | | |
| 2 | 90-104 | 10 | 282 | | no GC | | |
| 3 | 104-108 | 5 | 132 | 0.00 | 4.22 | 95.78 | 0.0 |
| 4 | 108 | 1 | 72 | 0.00 | 2.70 | 97.30 | 0.0 |
| 5 | 108 | 1 | 54 | 0.00 | 2.06 | 97.94 | 0.0 |
| 6 | 108 | 1 | 62 | 0.00 | 3.17 | 96.76 | 0.1 |
| 7 | 108 | 1 | 48 | 0.00 | 1.86 | 98.14 | 0.0 |
| 8 | 108 | 1 | 125 | 0.00 | 0.88 | 99.12 | 0.0 |
| 9 | 109 | 1 | 78 | 0.00 | 0.46 | 99.54 | 0.0 |
| 10 | 108 | 1 | 65 | 0.00 | 0.32 | 99.63 | 0.0 |
| 11 | 109 | 1 | 82 | 0.00 | 0.26 | 99.74 | 0.0 |
| 12 | 109 | 1 | 73 | 0.00 | 0.04 | 99.96 | 0.0 |
| 13 | 109 | 1 | 265 | 0.00 | 0.02 | 99.96 | 0.0 |
| 14 | 109 | 1 | 406 | 0.00 | 0.05 | 99.95 | 0.0 |
| 15 | 109 | 1 | 433 | 0.00 | 0.00 | 99.99 | 0.0 |
| 16 | 109 | 1 | 325 | 0.00 | 0.00 | 99.94 | 0.1 |
| Sump | | | 90 | 0.00 | 0.00 | 87.74 | 12.3 |

*$t_R$ = retention time

For examples 2 to 4, the following procedures were used.

The experiments were carried out in an absorption unit (semi-batch system), comprising a stirred autoclave to which gas could be fed in up-flow mode, and a condenser. The autoclave was equipped with a pressure gauge and a type J thermocouple. A safety rupture disc was attached to the autoclave head. A high wattage ceramic fiber heater was used to supply heat to the autoclave. The gas flows were regulated by mass flow controllers (from Brooks Instrument) and the temperature of the condenser was maintained by a chiller. The maximum working pressure and temperature were 1000 psi (69 bar) and 350° C., respectively.

During runs at atmospheric pressure, the pH of the solution was monitored in situ by using a pH probe (from Cole-Parmer), which was installed in the bottom of the autoclave. This pH probe was limited by a maximum temperature and pressure of 135° C. and 100 psi, respectively. Therefore, before carrying out experiments at a pressure above atmospheric pressure ("higher pressure"), the pH probe was removed and the autoclave was capped. In both cases (atmospheric pressure and higher pressure), liquid samples were collected by directly attaching a vial (atmospheric pressure) or a stainless steel cylinder filled with caustic (higher pressure) to the sampling system. A specifically designed LabVIEW program was used to control the absorption unit operation and to acquire experimental data like temperature, pressure, stirrer speed, pH (at atmospheric pressure), gas flow rate and off-gas concentration.

The gas mixture used in the examples had the following properties:
Gas feed composition: 10 mol-% $CO_2$, 1 mol-% $H_2S$, 89 mol-% $N_2$
Gas flow rate: 154 SCCM
Temperature: 40.8° C.
Pressure: 1 bar
Volume: 15 mL (i=0.1 min)
Stirring rate: 200 rpm The experiments of examples 2 to 4 were performed by flowing gas mixtures as specified above through the autoclave. The autoclave was previously loaded with the respective aqueous amine solution, as specified below. The acid gas mixture was fed to the bottom of the reactor. The gases leaving the autoclave were passed through the condenser, which was kept at 10° C., in order to remove any entrained liquids. A slip-stream of the off-gas leaving the condenser was fed to a micro-gas-phase chromatograph (micro-GC, from Inficon) for analysis while the main gas flow passed through a scrubber. After reaching breakthrough, nitrogen was used to purge the system.

The slip-stream of the off-gas was analyzed using a custom-built micro-GC. The micro-GC was configured as a refinery gas analyzer and included 4 columns (Mole Sieve, PLOT U, OV-1, PLOT Q) [by Aglient] and 4 thermal conductivity detectors. A portion of the off-gas was injected into the micro-GC approximately every 2 min. A small internal vacuum pump was used to transfer the sample into the micro-GC. The nominal pump rate was approximately 20 mL/min in order to achieve 10× the volume of line flushes between the sample tee and the micro GC. The actual amount of gas injected into the GC was approximately 1 μL. The PLOT U column was used to separate and identify $H_2S$ and $CO_2$, and the micro-TCD was used to quantify them.

M3ETB with a purity of 99% was used to obtain the different aqueous solutions described below.

The term "acid gas loading" as used herein stands for the concentration of the $H_2S$ and $CO_2$ gases physically dissolved and chemically combined in the absorbent solution as expressed in moles of gas per moles of the amine.

EXAMPLE 2

Figure 2:
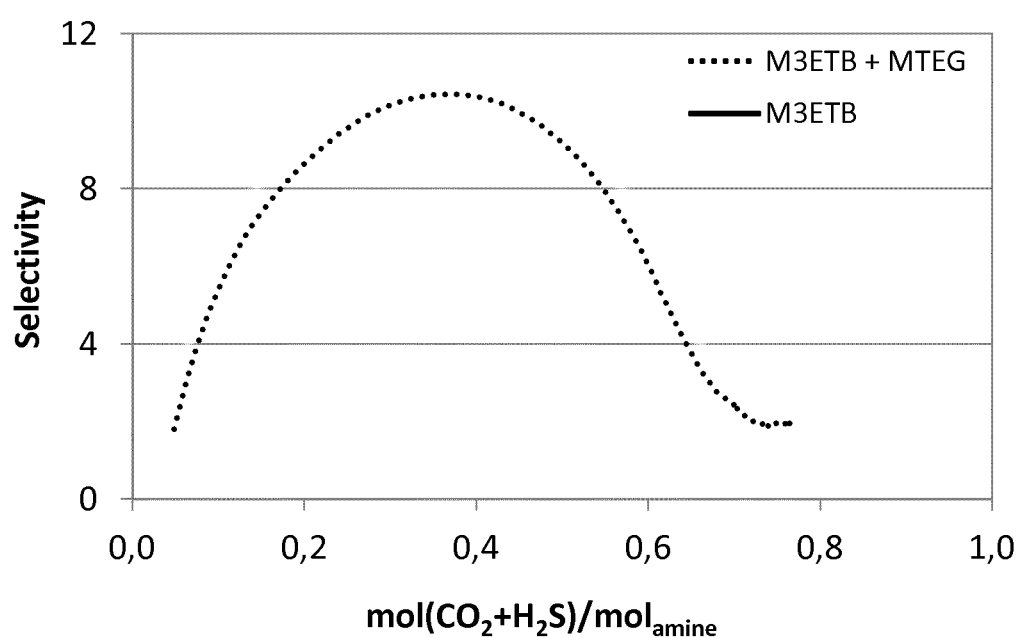
FIG. 2 is a plot of the selectivity of $H_2S$ over $CO_2$ as a function of acid gas loading of an aqueous solution of methoxyethoxyethoxyethyl-tert-butylamine (M3ETB, 30 weight-%) and an aqueous solution of M3ETB (30 weight-%) and methyltriethylene glycol (MTEG, 10 weight-%).
Figure 3:
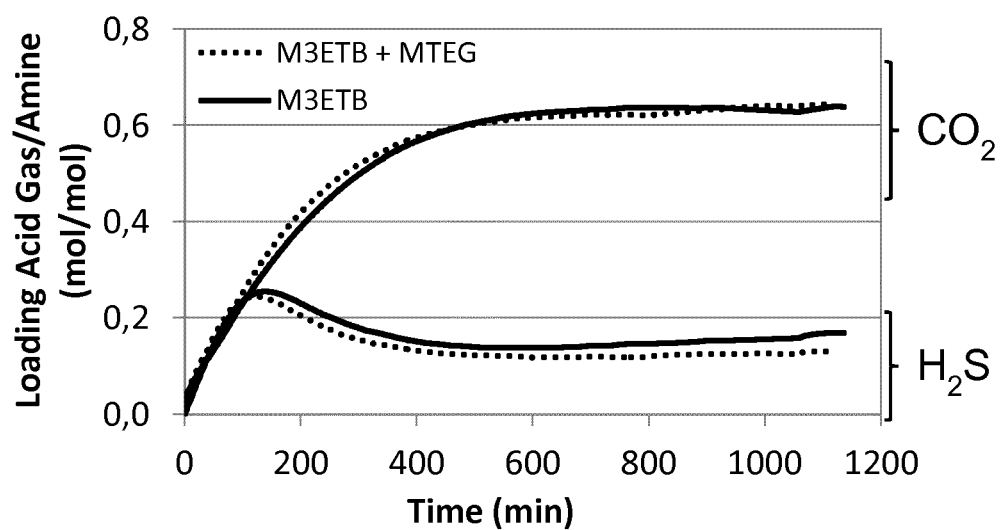
FIG. 3 is a plot of the acid gas loading over time of an aqueous solution of M3ETB (30 weight-%) and an aqueous solution of M3ETB (30 weight-%) and MTEG (10 weight-%).

An aqueous solution of M3ETB (30 weight-%) was compared to an aqueous solution comprising M3ETB (30 weight-%) and MTEG (10 weight-%). The acid gas loading over time was determined, as well as the selectivity of $H_2S$ over $CO_2$ as a function of acid gas loading. The results are shown in FIGS. 2 and 3.

Aqueous M3ETB has a maximum selectivity of about 11 at a loading of about 0.35 moles. The selectivity declines at higher $H_2S$ and $CO_2$ loadings. It was shown that the presence of MTEG has only a minor impact on selectivity, with a maximum selectivity of about 10 and the maximum not shifted to lower loadings.

The acid gas loading of aqueous M3ETB over time shows a maximum $CO_2$ loading of about 0.62 moles of $CO_2$ per mole of amine after about 600 minutes, while the $H_2S$ loading rises to a maximum of about 0.25 moles of $H_2S$ per mole of amine after about 150 minutes, afterwards falling to about 0.15 moles of $H_2S$ per mole of amine at about 400 minutes and remaining essentially steady afterwards. Probably, bound $H_2S$ is displaced by $CO_2$ at higher loadings. The presence of MTEG has only a minor impact on acid gas loading over time, following the same trend with a slightly lower $H_2S$ loading from about 150 minutes onwards.

EXAMPLE 3

Figure 4:
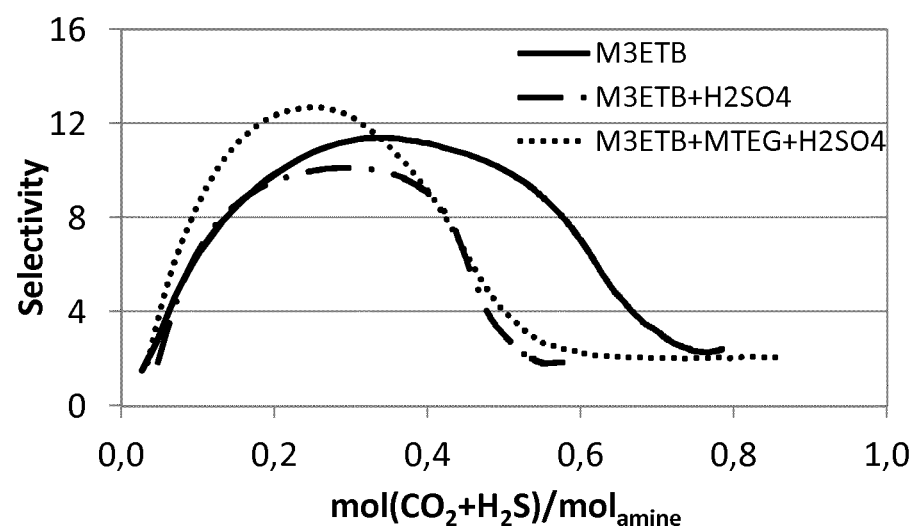
FIG. 4 is a plot of the selectivity of $H_2S$ over $CO_2$ as a function of acid gas loading of an aqueous solution of M3ETB (30 weight-%), an aqueous solution of M3ETB (30 weight-%) and $H_2SO_4$ (2 weight-%), and an aqueous solution of M3ETB (30 weight-%), MTEG (10 weight-%) and $H_2SO_4$ (2 weight-%).

An aqueous solution of M3ETB (30 weight-%) was compared to an aqueous solution of M3ETB (30 weight-%) and $H_2SO_4$ (2 weight-%), and an aqueous solution of M3ETB (30 weight-%), MTEG (10 weight-%) and $H_2SO_4$ (2 weight-%). The acid gas loading over time was determined, as well as the selectivity of $H_2S$ over $CO_2$ as a function of acid gas loading. The results are shown in FIGS. 4 and 5.

As discussed in example 2, aqueous M3ETB has a maximum selectivity of about 11 at a loading of about 0.35 moles, which declines at higher $H_2S$ and $CO_2$ loadings. Addition of $H_2SO_4$ leads to a decrease of the maximum selectivity to about 10 and a shift of the maximum towards lower loadings of about 0.30 moles. The presence of $H_2SO_4$ and MTEG leads to an increase of selectivity to about 13 and a slight shift of the maximum towards lower loadings of about 0.25 moles.

Figure 5:
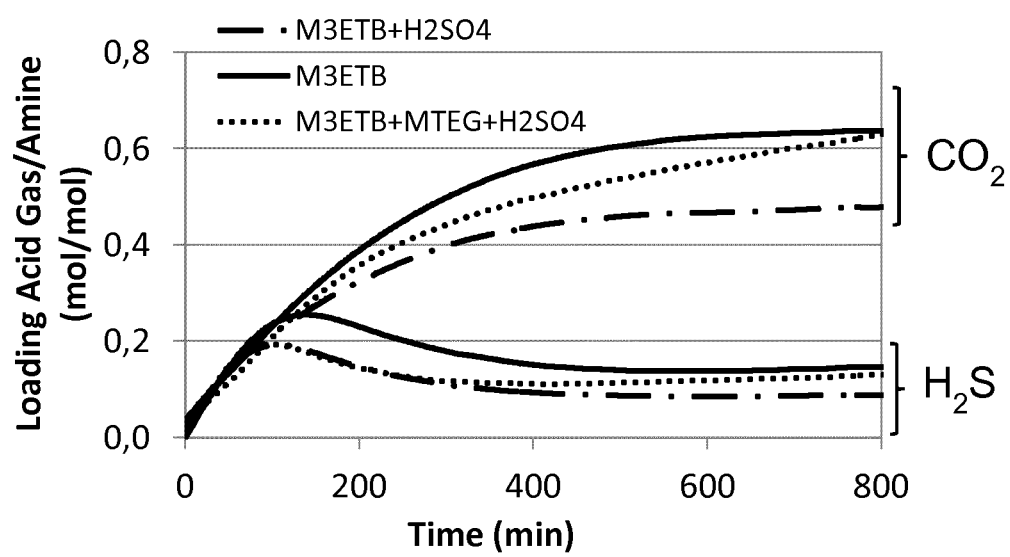
FIG. 5 is a plot of the acid gas loading over time of an aqueous solution of an aqueous solution of M3ETB (30 weight-%), an aqueous solution of M3ETB (30 weight-%) and $H_2SO_4$ (2 weight-%), and an aqueous solution of M3ETB (30 weight-%), MTEG (10 weight-%) and $H_2SO_4$ (2 weight-%).

FIG. 5 shows that the addition of $H_2SO_4$ to an aqueous solution of M3ETB decreases acid gas capacity. In the case of $CO_2$, the maximum loading is about 0.47 moles of $CO_2$ per mole of amine as compared to 0.62 moles of $CO_2$ per mole of amine without $H_2SO_4$. In the case of $H_2S$, the final $H_2S$ loading is about 0.10 moles of $H_2S$ per mole of amine at about 250 minutes as compared to about 0.15 moles of $H_2S$ per mole of amine at about 400 minutes without $H_2SO_4$.

An aqueous solution of M3ETB, MTEG and $H_2SO_4$ displays an acid gas loading between that of an aqueous solution of M3ETB and that of an aqueous solution of M3ETB and $H_2SO_4$.

EXAMPLE 4

Figure 6:
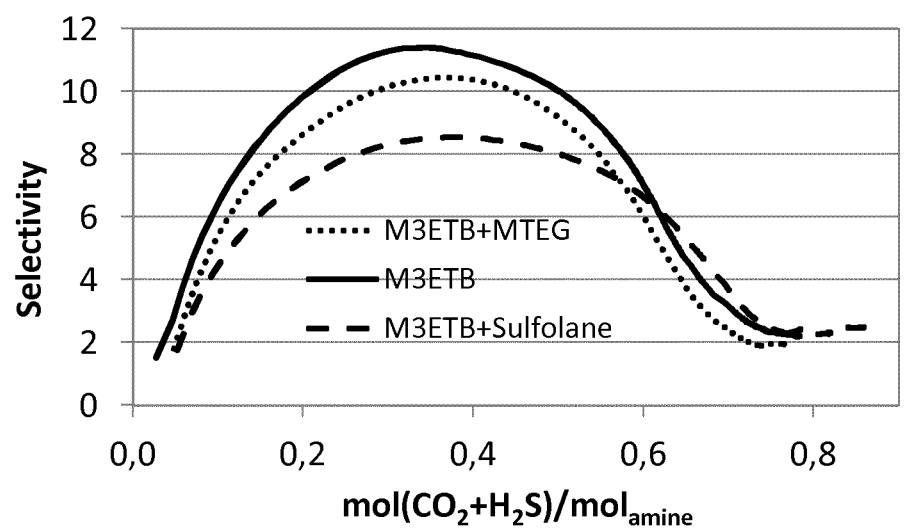
FIG. 6 is a plot of the selectivity of $H_2S$ over $CO_2$ as a function of acid gas loading of an aqueous solution of M3ETB (30 weight-%), an aqueous solution of M3ETB (30 weight-%) and MTEG (10 weight-%), and an aqueous solution of M3ETB (30 weight-%) and sulfolane (10 weight-%).
Figure 7:
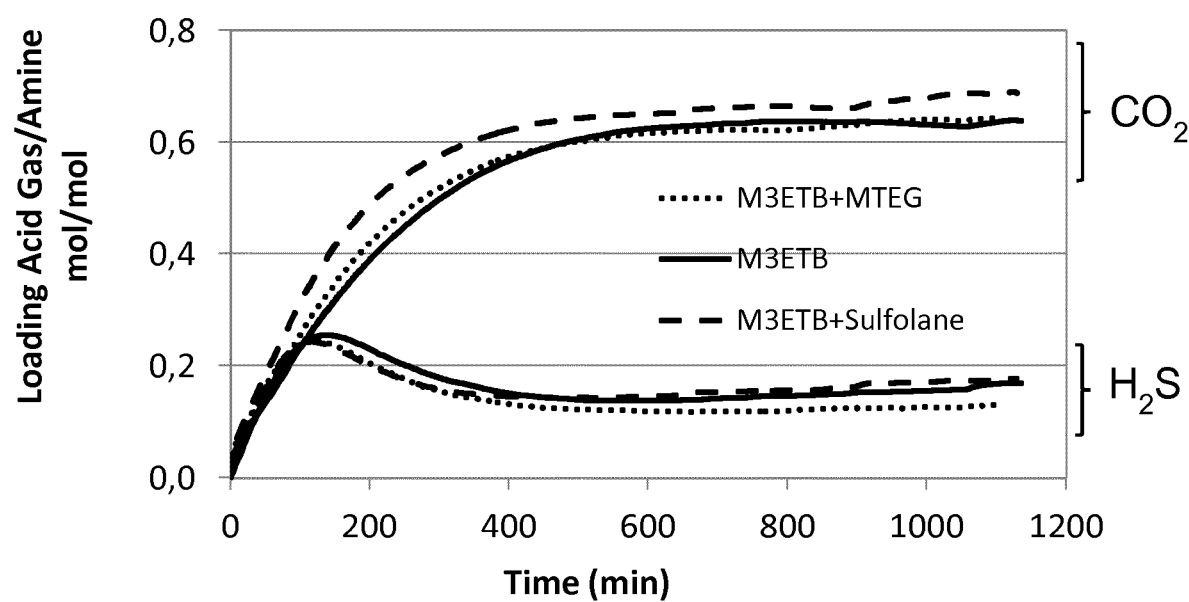
FIG. 7 is a plot of the acid gas loading over time of an aqueous solution of an aqueous solution of M3ETB (30 weight-%), an aqueous solution of M3ETB (30 weight-%) and MTEG (10 weight-%), and an aqueous solution of M3ETB (30 weight-%) and sulfolane (10 weight-%).

An aqueous solution of M3ETB (30 weight-%) and MTEG (10 weight-%) was compared to an aqueous solution of M3ETB (30 weight-%) and sulfolane (10 weight-%). The acid gas loading over time was determined, as well as the selectivity of $H_2S$ over $CO_2$ as a function of acid gas loading. The results are shown in FIGS. 6 and 7.

The aqueous solution of M3ETB and MTEG has a maximum selectivity of about 10. The aqueous solution of M3ETB and sulfolane has a maximum selectivity of about 8.5.

EXAMPLE 5

To determine the critical solution temperature, a miscibility unit was applied. This unit allows the measurement of the temperature at which phase separation occurs ("critical solution temperature").

The unit comprised a sight class vessel equipped with a pressure gauge and a thermocouple. A heater was used to supply heat to the vessel. Measurements are possible up to a temperature of 140° C. The possible phase separation could be visually observed via the sight glass. In the following table, the measured critical solution temperatures are shown for different mixtures with the amine M3ETB.

| Aqueous Solutions | Critical Solution Temperature |
|---|---|
| 36 wt.-% M3ETB | 107° C. |
| 30 wt.-% M3ETB + 5 wt.-% MTEG | 128 to 130° C. |
| 30 wt.-% M3ETB + 5 wt.-% MTEG + 1.6 wt.-% $H_3PO_4$ | 124° C. |
| 30 wt.-% M3ETB + 10 wt.-% MTEG + 1.6 wt.-% $H_3PO_4$ | —* |
| 30 wt.-% M3ETB + 10 wt.-% MTEG + 2 wt.-% $H_2SO_4$ | —* |

-continued

| Aqueous Solutions | Critical Solution Temperature |
|---|---|
| 30 wt.-% M3ETB + 10 wt.-% MTEG + 4 wt.-% $H_2SO_4$ | —* |
| 25 wt.-% M3ETB + 8.3 wt.-% MTEG + 2 wt.-% $H_2SO_4$ | —* |
| 35 wt.-% M3ETB + 11.7 wt.-% MTEG + 2 wt.-% $H_2SO_4$ | —* |
| 30 wt.-% M3ETB + 10 wt.-% Sulfolane + 2 wt.-% $H_2SO_4$ | —* |
| 30 wt.-% M3ETB + 5 wt.-% Sulfolane + 2 wt.-% $H_2SO_4$ | 137 to 139° C. |
| 30 wt.-% M3ETB + 10 wt.-% MDEA + 2 wt.-% $H_2SO_4$ | 129° C. |

*no phase separation observed at up to 140° C.

The invention claimed is:

1. An absorbent for the selective removal of hydrogen sulfide from a fluid stream comprising carbon dioxide and hydrogen sulfide, wherein the absorbent contains an aqueous solution, comprising:
a) an amine or a mixture of amines of the general formula (I)

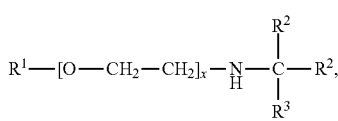

wherein $R^1$ is $C_1$-$C_5$-alkyl; $R^2$ is $C_1$-$C_5$-alkyl; $R^3$ is selected from hydrogen and $C_1$-$C_5$-alkyl; x is an integer from 2 to 10; and
b) an ether or a mixture of ethers of the general formula (II);

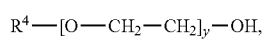

wherein $R^4$ is $C_1$-$C_5$-alkyl; and y is an integer from 2 to 10;
wherein $R^1$ and $R^4$ are identical;
wherein the mass ratio of b) to a) is from 0.08 to 0.5.

2. The absorbent according to claim 1, wherein the number average of x and the number average of y do not differ from each other by more than 1.0.

3. The absorbent according to claim 2, wherein x and y are identical.

4. The absorbent according to claim 3, wherein x and y are 3.

5. The absorbent according to claim 1, wherein
the amine a) is selected from (2-(2-tert-butylaminoethoxy)ethyl)methyl ether, (2-(2-isopropyl-aminoethoxy)ethyl)methyl ether, (2-(2-(2-tert-butylaminoethoxy)ethoxy)ethyl)methyl ether, (2-(2-(2-isopropylaminoethoxy)ethoxy)ethyl)methyl ether, (2-(2-(2-tert-butylaminoethoxy)-ethoxy)ethoxy)ethyl)methyl ether, and (2-(2-(2-(2-Isopropylaminoethoxy)ethoxy)ethoxy)-ethyl)methyl ether; and
the ether b) is selected from 2-(2-methoxyethoxy)ethanol, 2-(2-(2-methoxyethoxy)ethoxy)-ethanol, and 2-(2-(2-(2-methoxyethoxy)ethoxy)ethoxy)ethanol.

6. The absorbent according to claim 5, wherein the amine a) is (2-(2-(2-tert-butyl-aminoethoxy)ethoxy)ethyl)methyl ether and the ether b) is 2-(2-(2-methoxyethoxy)-ethoxy)ethanol.

7. The absorbent according to claim 1, wherein the mass ratio of b) to a) is from 0.15 to 0.35.

8. The absorbent according to claim 1, wherein the absorbent comprises an acid c).

9. A process for the production of absorbent according to claim 1, wherein an ether of formula (II) is reacted with a primary amine of the general formula (III)

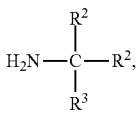

wherein $R^2$ is $C_1$-$C_5$-alkyl and $R^3$ is selected from hydrogen and $C_1$-$C_5$-alkyl;
to form an amine of formula (I), wherein the ether of formula (II) is not completely consumed in the reaction and the ether of formula (II) is not fully separated from the amine of formula (I).

10. The process according to claim 9, wherein the molar amount of the primary amine of formula (III) exceeds the molar amount of the ether of formula (II) during the reaction.

11. The process according to claim 9, wherein the reaction is carried out in the presence of a hydrogenation/dehydrogenation catalyst.

12. A process for the selective removal of hydrogen sulfide from a fluid stream comprising carbon dioxide and hydrogen sulfide, in which the fluid stream is contacted with the absorbent according to claim 1, wherein a laden absorbent and a treated fluid stream are obtained.

13. The process according to claim 12, wherein the laden absorbent is regenerated by means of at least one of the measures of heating, decompressing and stripping with an inert fluid.

* * * * *

UNITED STATES PATENT AND TRADEMARK OFFICE
CERTIFICATE OF CORRECTION

PATENT NO.        : 11,241,652 B2
APPLICATION NO.   : 16/612921
DATED             : February 8, 2022
INVENTOR(S)       : Martin Ernst Page 1 of 1

It is certified that error appears in the above-identified patent and that said Letters Patent is hereby corrected as shown below:

On the Title Page

(73) Assignees: BASF SE (REITSTÖTTER, KINZEBACH & PARTNER), Ludwigshafen am Rhein (DE); ExxonMobil Research and Engineering Company, Annandale, NJ (US) should read BASF SE, Ludwigshafen am Rhein (DE); ExxonMobil Research and Engineering Company, Annandale, NJ (US)

Signed and Sealed this
Eleventh Day of February, 2025

Coke Morgan Stewart
*Acting Director of the United States Patent and Trademark Office*